United States Patent
Elman

(10) Patent No.: US 7,224,453 B2
(45) Date of Patent: May 29, 2007

(54) DEVICE, METHOD AND SYSTEM FOR DETERMINING THE ROAD SURFACE CONDITION

(76) Inventor: Ulf Elman, Bjornstigen 8, Solna (SE) 170 72

( * ) Notice: Subject to any disclaimer, the term of this patent is extended or adjusted under 35 U.S.C. 154(b) by 124 days.

(21) Appl. No.: 10/530,191

(22) PCT Filed: Oct. 9, 2003

(86) PCT No.: PCT/SE03/01570

§ 371 (c)(1),
(2), (4) Date: Apr. 4, 2005

(87) PCT Pub. No.: WO2004/034349

PCT Pub. Date: Apr. 22, 2004

(65) Prior Publication Data

US 2006/0050270 A1    Mar. 9, 2006

(30) Foreign Application Priority Data

Oct. 10, 2002    (SE) .................................. 0202987

(51) Int. Cl.
*G01J 3/28*    (2006.01)
(52) U.S. Cl. .................................................... 356/326
(58) Field of Classification Search ...................... None
See application file for complete search history.

(56) References Cited

U.S. PATENT DOCUMENTS

| | | | |
|---|---|---|---|
| 4,274,091 A | 6/1981 | Decker | |
| 5,218,206 A | 6/1993 | Schmitt et al. | |
| 5,557,261 A * | 9/1996 | Barbour | 340/580 |
| 5,962,853 A | 10/1999 | Huth-Fehre et al. | |
| 6,166,645 A | 12/2000 | Blaney | |
| 6,356,350 B1 | 3/2002 | Silver et al. | |
| 6,459,083 B1 * | 10/2002 | Finkele et al. | 250/339.11 |

OTHER PUBLICATIONS

Bullok, A. M., et al, LEOS '97 10th annual meeting, vol. 2, pp. 550-551, 1997.

Hovde, C. et al, Electronic-Enhanced Optics, Optical Sensing in Semiconductor Manufacturing, Electro-Optics in Space, Broadband.

Networks, 2000. Digest of the LEOS summer Topical Meetings, pp. II11-II12, 2000.

* cited by examiner

*Primary Examiner*—Tu T. Nguyen

(57) ABSTRACT

The invention relates to a device, a method and a system for determining a road surface condition, where the surface condition is one of dry, wet or icy. The device comprises a reflectance spectrometer which senses the reflectance properties of the road at one or several wavelengths and uses these reflectance properties to determine the surface condition. The reflectance spectrometer is a wavelength modulation spectrometer, preferably for the near infrared region. The system determines the surface condition and indicates it to a user of the system.

10 Claims, 3 Drawing Sheets

DEVICE, METHOD AND SYSTEM FOR DETERMINING THE ROAD SURFACE CONDITION

CROSS REFERENCE TO RELATED APPLICATIONS

This application is a national stage application of International Application PCT/SE2003/001570, filed Oct. 9, 2003, designating the United States of America, which claims the benefit of Swedish Patent Application No. SE-0202987-C2, filed Oct. 10, 2002.

The present invention relates to a system, a device and a method for determining the presence or absence of liquid water or ice according to the introductory portions of the independent claims. In particular, it relates to such a system, device and method using wavelength modulation spectroscopy.

BACKGROUND OF THE INVENTION

A number of solutions for solving the problem of determining possible slipperiness of road surfaces, in particular aimed at detecting presence or absence of water or ice on the road surface, are known. Older methods for determining the road surface condition using mechanical arrangements are known but are prone to faults and wear. A number of solutions to the problem of detecting water or ice on a road surface at a fixed position have also been suggested, but are generally not applicable to the problem of determining the road surface condition at or near a moving vehicle. For that problem, remote sensing methods using spectroscopical methods have become the dominating solution, and in particular near infrared spectroscopical methods due to the distinct spectroscopical properties of liquid and frozen water in that wavelength interval.

One of the earliest patents relating to this subject is U.S. Pat. No. 4,271,091 (1981) wherein a method of detecting ice on road surfaces by detecting an amplitude modulated light beam in the infrared region reflected from the road surface is disclosed. The method suffers from the drawback that there is no provision for separating reflectance changes occurring due to presence of ice from those occurring due to presence of water on the road surface, or due to changes in the reflectance properties of the asphalt or concrete constituting the road paving.

U.S. Pat. No. 5,218,206 (1990) discloses a method of detecting ice or water on road surfaces by detecting the reflectance of the road surface at two separate wavelengths in the infrared region. The method calculates the ratio between the two reflectances, and indicates the presence of water if the ratio exceeds a certain level or the presence of ice if the ratio falls below a certain level. If the ratio remains within an intermediate level, the method indicates that the road surface is dry, but unfortunately the ratio may also fall within this intermediate range if certain proportions of water and ice are present at the road surface.

Assuming the reflectance to be influenced by three parameters only; road paving reflectivity, effective liquid water layer thickness and effective ice layer thickness, three independent parameters need to be measured, and a number of solutions using three or more wavelengths have been suggested, i.a. U.S. Pat. No. 5,962,853, proposing detection at at least four wavelengths. Unfortunately, the absorption of light in non turbid media adheres to the Beer-Lambert law, stating that the transmission through the medium decreases exponentially with increasing layer thickness. For a detection system with finite signal dynamics, this corresponds to a very limited dynamic range in terms of layer thickness variations. To solve this problem, one may detect the presence of water or ice using several different wavelength intervals having different absorption coefficients, where detection in each interval gives a reliable indication of water or ice presence for a range of substance thicknesses. Combining results from measurements in several such intervals, an acceptable total layer thickness tolerance is achieved. Unfortunately, this implies detecting reflectances at a comparatively large number of wavelengths, necessitating a complex, and therefore expensive arrangement.

Wavelength modulation spectroscopy is a particular form of spectroscopy where the used light wavelength is modulated at a frequency f. After interfering with a substance, usually a gas, the wavelength modulation gives rise to amplitude modulation at frequencies being multiples of the wavelength modulation frequency f, and the amplitude modulated signal at one of these multiples of f is used for detection. With wavelength modulation spectroscopy it is possible to achieve higher signal to noise ratio than with other corresponding spectroscopical methods, thus making it possible to detect and measure substances in smaller concentrations than otherwise. In U.S. Pat. No. 6,356,350 a form of wavelength modulation spectroscopy is disclosed, where signals are detected at more than one of these multiples of f concurrently, and the signals received are used to calculate properties of a gas being measured, such as its concentration, temperature or pressure. The document does however not disclose a method of concurrently measuring the amount of two or more substances with overlapping spectral features, using a single detected modulated wavelength. Neither does the document disclose a method of deriving information on whether the substance being detected is turbid or not.

An object of the invention is therefore to provide a system, a method and a device which overcome the above mentioned problems with prior art surface condition detection devices.

These and other objects are attained by a system, a method and a device according to the characterising portions of the independent claims.

SUMMARY OF THE INVENTION

The invention relates to a device for determining a road surface condition, where the surface condition is one of dry, wet or icy. The device comprises a reflectance spectrometer which senses the reflectance properties of the road at one or several wavelength and uses these reflectance properties to determine the surface condition. The reflectance spectrometer is a wavelength modulation spectrometer, preferably for the near infrared region. The device may wavelength modulate the light being reflected by the surface before or after hitting the surface. The device uses light at a chosen wavelenght, being wavelength modulated at a frequency f, and detects the resulting amplitude modulation of the light at more than one multiple of f, using the amplitude of the amplitude modulations at different multiples of f for determining the road surface condition.

The device may sense the reflectance properties of a surface at more than one wavelength and use the additional information on the reflectance properties to determine the structural properties of the detected liquid water or ice, i.e. determining whether the water or ice is clear or turbid. This information about the structural properties may be used to assess the slipperiness of the surface.

The invention further relates to a method for determining a road surface condition using wavelength modulation spectroscopy, and yet further to a system for determining and indicating a surface condition to a user of the system.

DESCRIPTION OF PREFERRED EMBODIMENTS

Figure 1:
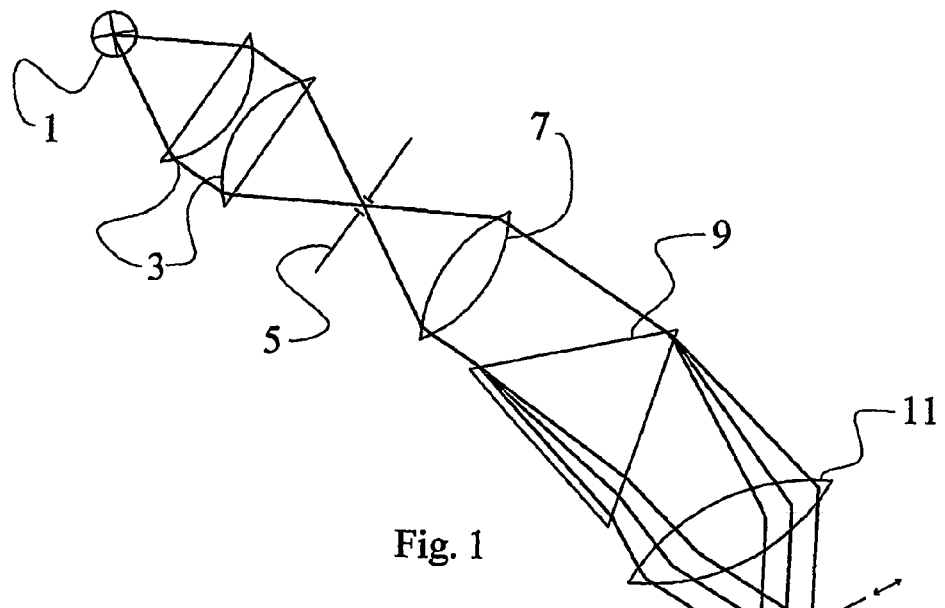
FIG. 1 shows a first embodiment of the ice and water detection device.

FIG. 1 shows a first embodiment of the ice and water detection device which uses prisms as dispersing elements. The embodiment comprises a light beam emitter with suitable optical properties, constituted by a light source 1, and a first focusing element 3 focusing a portion of the light emitted by the light source on an aperture 5. The light source 1 is schematically shown as an incandescent lamp, and the first focusing element 3 is drawn as a pair of planoconvex lenses, but this is chosen only for illustrating the fundamental function of the device.

The diverging light beam emitted from the aperture 5 is then transmitted towards a first wavelength selective system. In the wavelength selective system the beam is collimated by a first lens 7, and the collimated beam is directed through a first dispersing prism 9. The light beam transmitted through the prism is dispersed into a range of wavelengths, which are focused by a second lens 11 onto a selection element 13 which only transmits selected segments of the light focused onto it. The selection element 13 is here embodied as a chopper wheel 24, shown in FIG. 3. The primary function of the chopper wheel 24 is to transmit selected portions of the light of the continuous range of wavelengths focused onto it, through three non-circular apertures 26, 28, 30. As the chopper wheel 24 is rotated, the portion of the apertures 26, 28, 30 exposed to the light focused onto it shifts, as indicated by the arrow in the drawing, thereby selecting a changing set of wavelengths being transmitted through the chopper wheel 24. Three diverging light beams transmitted through the chopper wheel 24 are again focused by a third lens 15, and the collimated beams enter a second dispersing prism 17. Using a second dispersing prism 17 with dispersing properties identical to that of the first dispersing prism 9, the three collimated beams emerge from the second dispersing prism 17 overlapping each other and being parallel.

The beam emitted from the second dispersing prism 17 is partially transmitted through a beam splitter 19, and hits the road surface. Light reflected from the road surface hitting the beam splitter 19, is partially reflected by the beam splitter 19 and transmitted in a direction orthogonal to that of the outgoing beam. The reflected beam is then focused by a fourth lens 21 onto a detector 23, detecting the signal from the road surface.

The detector could for example be an InGaAs, Ge, InAs, PbS or a pyroelectric detector. The advantage of pyroelectric detectors, as compared to the others, is the lower cost and its flat spectral response, but it does have a detectivity two to four orders of magnitude lower than the other detector types. The total light throughput of the system is related to the dispersive power of the dispersive element, i.e. the prisms shown in the embodiment above. Even with prisms made of substances which are highly dispersive in the wavelength range of interest, such as Si or one of the Irtran glasses, the light throughput may be insufficient for using low detectivity detectors.

Figure 2:
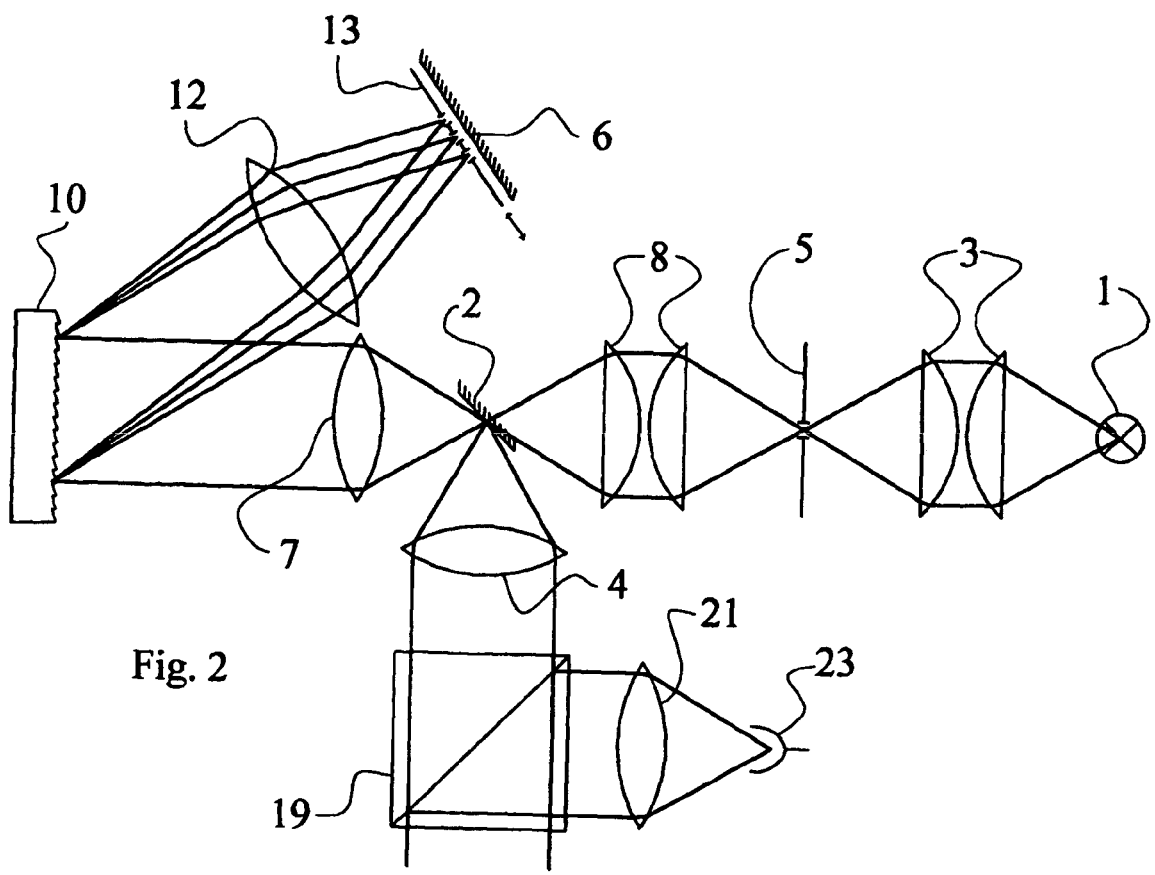
FIG. 2 shows a second embodiment of the ice and water detection device.

FIG. 2 shows a second embodiment of the detection device which instead of prisms uses reflecting gratings, which have a much higher dispersive power, as dispersing elements. The embodiment comprises a light beam emitter identical to the one in FIG. 1, and the emitted light is focused by a second focusing element 8 drawn as a pair of planoconvex lenses. The focused beam passes, at its focal point, above a first mirror 2 (being positioned in a direction below the paper plane of the figure), and is then directed to a second wavelength selective system.

In the second wavelength selective system the beam is collimated by a first lens 7, and the collimated beam i directed towards a reflective grating 10. The light beam reflected from the grating is dispersed into a range of wavelengths, which are focused by a fifth lens 12 onto a selection element 13 which only transmits selected segments of the light focused onto it. The selection element 13 is here embodied as a chopper wheel 24, shown in FIG. 3. The three light beams transmitted through the chopper wheel 24 are reflected back through the chopper wheel 24 by a second mirror 6, slightly tilted downwards (in a direction out of the paper plane of the figure), are recollimated by the fourth lens 12, and are reflected back from the grating 10 overlapping each other and being parallel. The three overlapping beams are then focused by the first lens 7 onto the first mirror 2, which reflects the beams towards a sixth lens 4.

The sixth lens 4 collimates the beams and directs them to a set-up comprising a beam splitter 19, a fourth lens 21 and a detector 23, identical to the one in the first embodiment.

Obviously, the embodiment could alternatively have been arranged with a transmission grating, while a set-up similar to the first embodiment, having two gratings, would be unnecessary due to the potentially high dispersive power of the gratings, and inconvenient due to the cost of gratings. The higher optical throughput of the system does on the other hand makes it possible to use cheaper detectors with lower detectivity.

In this embodiment the wavelength selection element 13 could alternatively have been embodied as a set of tuning fork type optical choppers, which are essentially mirrors mounted on the ends of electromechanically driven tuning forks. The fork may resonate at a higher frequency than a rotating disc type chopper device, and may, if driven at its resonance frequency, be very insensitive to disturbances. This kind of chopper also has a longer life span, but may be more expensive.

Figure 3:
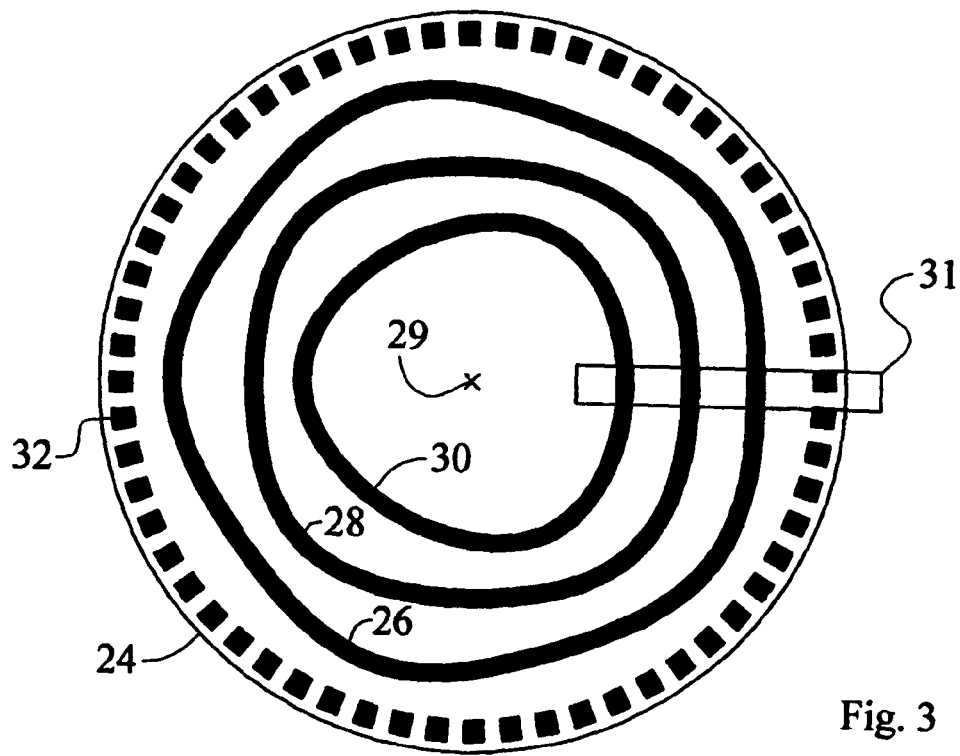
FIG. 3 shows an embodiment of a chopper wheel usable in the first and second embodiments.

FIG. 3 shows an embodiment of a chopper wheel 24 usable in the first and second embodiments. The solid areas on the chopper wheel 24 indicate apertures in the otherwise non transparent chopper wheel 24. A portion of the non circular rings 26, 28, 30 indicated by the area 31 is what is illustrated in cross section in FIGS. 2 and 3 as the wavelength selection element 13. As the chopper wheel 24 rotates, the distance from the apertures to the center axis 29 of the chopper wheel 24 will shift back and forth periodically, with different periodicity for the different non circular rings 26, 28 and 30. The innermost non circular ring 30 moves back and forth three times per rotation of the wheel 24, the next ring 28 four times and the outermost non circular ring 26 five times per rotation.

The non circular rings 26, 28, 30 will thus select light beams at separate wavelengths, and as the wheel 24 rotates, the first wavelength selective system will emit a beam of light of three different wavelengths, each wavelength modulated at three, four and five times the rotational frequency of the wheel 24.

Any constant intensity wavelength modulated light beam experiencing wavelength dependent absorption will become amplitude modulated at frequencies corresponding to multiples of the wavelength modulation frequency. The DC signal will be proportional to the reflectance itself, i.e. the zeroeth derivative of the absorption with respect to the wavelength, the size of the amplitude modulation at the wavelength modulation frequency will be proportional to the derivative of the absorption with respect to the wavelength, and the size of the amplitude modulation at twice the wavelength modulation frequency will be proportional to the second derivative of the absorption with respect to the wavelength etc.

As water and ice have absorptions with different wavelength dependencies, a wavelength modulated light beam being transmitted though water or ice will become amplitude modulated in different ways, giving rise to different sets of amplitudes of the degree of amplitude modulation at different multiples of the wavelength modulation frequency. Assuming the wavelength dependence of the reflectance of the paving to be small or zero, ie. it has a flat absorption curve as a function of the wavelength, this will only give rise to a DC signal at the detector which may be neglected. Denoting the amplitude of the amplitude modulation at the frequency corresponding to the wavelength modulation frequency as $S_1$ and the amplitude of the amplitude modulation at twice the frequency corresponding to the wavelength modulation frequency as $S_2$, the relation between these amplitudes may be discussed using a diagrammatic approach.

Figure 4:
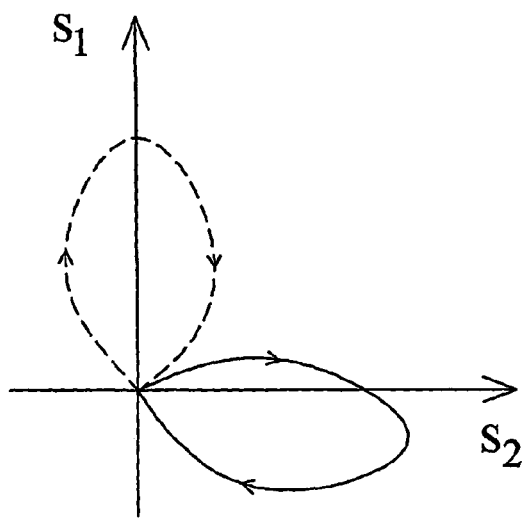
FIG. 4 shows theoretical signal values received for varying layer thicknesses.

Plotting $S_1$ and $S_2$ on the x- and y-axes of the graph in FIG. 4, respectively, for different ice (solid line) and water (dashed line) layer thicknesses at an arbitrarily chosen wavelength, curves similar to the ones shown in FIG. 4 may be found. For any substance, both $S_1$ and $S_2$ are obviously zero for a substance thickness of zero, and as the substance thickness increases, the curve deviates from the origin as indicated by the arrows on the curves. Eventually the substance thickness gets so large that the transmission through the substance approaches zero, and both curves then return to the origin. For an arbitrarily chosen wavelength, the proportions between $S_1$ and $S_2$ are not fixed, so the curves are loop-like. This may make it difficult to separate signals arising from presence of water from those arising from presence of ice, and if the curves cross it is for certain thicknesses not possible to separate them at all.

Figure 5:
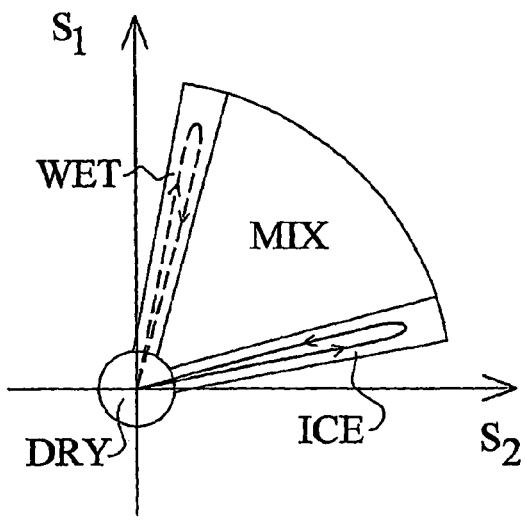
FIG. 5 shows how different signal value combinations are used to assess different surface conditions.

By choosing wavelength for detection properly, the proportions of $S_1$ and $S_2$ for both curves remain nearly fixed for any layer thickness, and the loops look nearly like straight lines extending in different directions from the origin of the graph, as in FIG. 5. The figure also shows how different parameter area sectors are interpreted as different surface conditions. An area DRY extending a small distance from the origin is interpreted as dry road surface, and two sectors ICE and WET extending along and including the loops corresponding to the ice signal loop and the water signal loop, are interpreted as purely icy and purely wet road surface, respectively. An area MIX extending between these last two areas is interpreted as a road surface covered by a mix of water and ice. The parameter area sectors outside these four areas may be used e.g. for fault tracing.

The radius of the circular area DRY within which the parameter values $S_1$ and $S_2$ are interpreted as indicating a dry surface, is defined by the noise level of the signal. The noise is caused by varying background reflection due to the graininess of the road surface, electronic noise and other factors. As the noise in the $S_1$ and $S_2$-parameters may be different and dependent, the DRY area might in practice be of any other shape but circular, the circular area chosen here is for simplicity only.

The width of the WET and ICE parameter areas is partially set by noise considerations, but also has to include factors such as temperature affecting the absorption curves for both water and ice, and salinity affecting the absorption curve for water. Increased salinity in water will affect the absorption curve for water in a way similar to a temperature increase, which may be interpreted as an increase in apparent temperature. Apparent temperature changes in the ranges present under normal circumstances for ice or water changes the absorption curves slightly, which in the $S_1$-$S_2$ plane appears as slight angular and other shifts of the ice and water curves.

Figure 6:
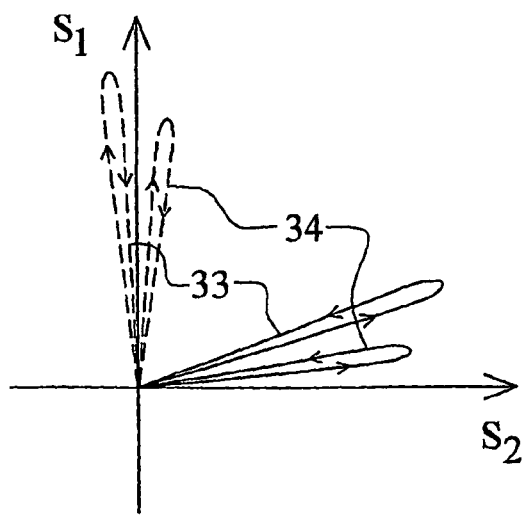
FIG. 6 shows theoretical signal values at different wavelengths.

FIG. 6 shows ice and water parameter curves for two different wavelengths, 33 and 34. Only two wavelengths are illustrated for simplicity reasons only, even though the first and second embodiments use three wavelengths. Several different wavelengths are found in the near infrared spectrum where the parameter curves are near linear, but for different wavelengths the curves may have different angular directions and extend different distances from the origin. Obviously, this needs to be compensated for, using different parameter area sectors for interpreting the road surface properties at different wavelengths. In the first and second embodiments of the inventions, the signals from which $S_1$ and $S_2$ are derived, are modulated at different frequencies, making it easy to apply different surface property interpretation rules. If a set of wavelengths is found where the parameter curves overlap, different interpretation rules may not be necessary, and the modulation frequencies at different wavelengths may be identical, simplifying the signal processing.

Preferably, the set of wavelengths used are chosen such that in the presence of clear water and/or ice a significant signal is received at at least one wavelength. This means that for the thinnest substance layers of interest, a signal is received at the most sensitive wavelength, i.e. the wavelength at which the absorptivity is the largest, while no signal is received at the other wavelength(s). As the substance layer thickness exceeds the interval where the most sensitive wavelength is active, i.e. where the substance appears completely intransparent at that wavelength, a signal is received at the next wavelength, while the substance still appears completely transparent at the next wavelength etc. A set of wavelengths should therefore be chosen such that any normally appearing clear substance layer thickness is detectable.

If the substances are not clear, however, the Beer-Lambert law is not adhered, and may be replaced by the Kubelka-Munk equations. Under such circumstances, appearing e.g. in the presence of dirty water or ice, snow, frost or slurries of water/ice mixtures, significant signal contributions may appear at several wavelengths simultaneously. This may be used to derive information on the structural properties of the water/ice layer on the road surface. From this information may be concluded the slipperiness of the ice/water layer, which may be presented to the user of the system according to the invention.

Figure 7:
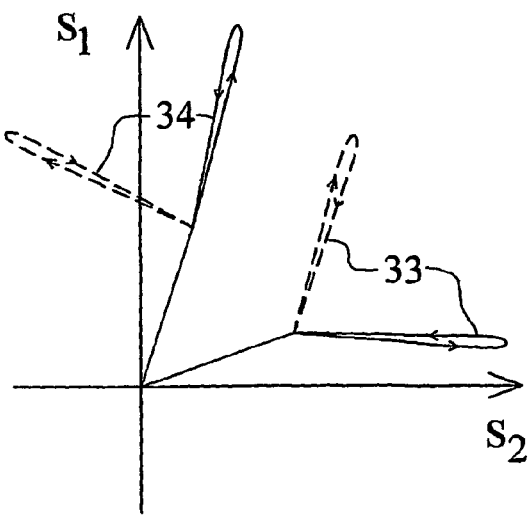
FIG. 7 shows theoretical signal values taking imperfections into account

FIG. 7 indicates the result of a further imperfection of the arrangement on the ice and water parameter curves. In FIGS. 4-7 it is assumed that the wavelength modulation causes no residual inherent amplitude modulation of the signal even in absence of water or ice, and the parameter curves thus starts and ends at the origin of the graphs. If such a residual amplitude modulation is present, the curves, here shown for two different wavelengths 33 and 34, will originate at different positions in the $S_1$-$S_2$ plane. Again, the result of such flaws may be compensated for using proper signal processing.

Figure 8:
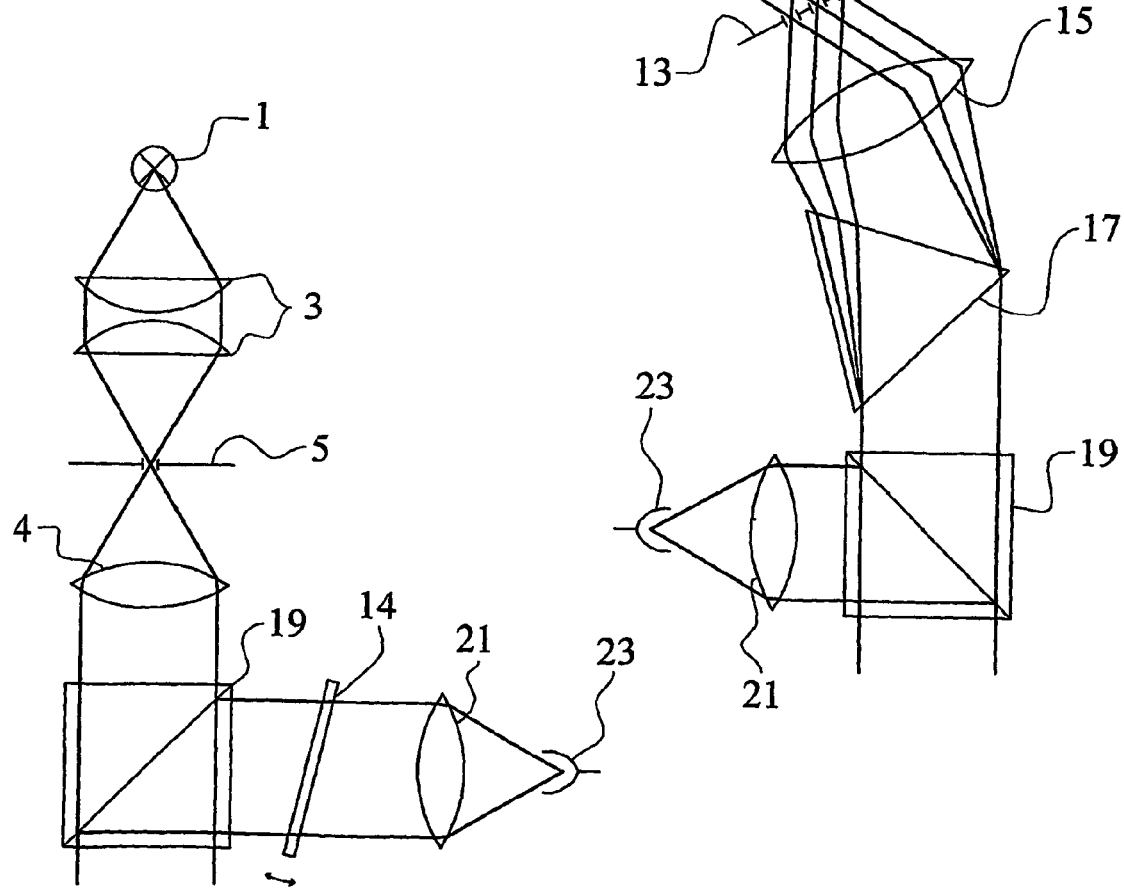
FIG. 8 shows a third embodiment of the ice and water detection device.

FIG. 8 shows a third embodiment of the detection device which instead of a dispersive element 9, 10, 17 and a wavelength selection element 13 uses a pivoting dielectric filter 14. Here, the wavelength modulation occurs after the light hitting the road surface has been received by the detection device. To be able to separate light originating from the light beam emitter of the detection device from background radiation, the aperture 5 of the light beam emitter is embodied as the aperture of a chopper wheel for intensity modulation. The result is that amplitude modulated light of a known frequency $f_A$ is emitted from the light beam emitter and may be separated from background radiation. The amplitude modulated light is then collimated by a sixth lens 4, partially transmitted through a beam splitter 19, and hits the road surface.

Light reflected from the road surface hitting the beam splitter 19, is partially reflected by the beam splitter 19 and transmitted in a direction orthogonal to that of the outgoing beam. The beam is then transmitted through a dielectric transmission filter 14, which is arranged at an angle slightly offset from the incoming beam. The filter angle is changed in a periodical manner, and the filter may for example be mounted on a galvanometer which periodically pivots the filter around an axis orthogonal to the beam direction, as indicated by the arrow in the figure. The filter is arranged to transmit a set of suitable wavelengths, and as the filter is tilted, these wavelengths shift. By vibrating the filter in a suitable way, the beam transmitted through the filter will be amplitude modulated at frequencies related to the vibration frequency of the filter. Through proper signal processing described below, the absorption properties of the road surface may be deduced. The beam is finally focused by a fourth lens 21 onto a detector 23.

In this embodiment, the signal parameters of interest, $S_1$ and $S_2$, are not found at the wavelength modulation frequency $f_\lambda$, and twice that frequency $2f_\lambda$, but at $f_A \pm f_\lambda$, and at $f_A \pm 2f_\lambda$. By selecting $f_A$ and $f_\lambda$, properly, $f_A \pm f_\lambda$ and $f_A \pm 2f_\lambda$ may be detected at conveniently low frequencies, allowing use of cheap, slow detectors. Meanwhile noise occurring as a result of the graininess of the road surface is picked up at $f_A$, allowing choice of $f_A$ at a low noise frequency.

In this embodiment there is no direct way of separating signals at different wavelengths by detecting them at different modulation frequencies, as all are wavelength modulated at the same frequency $f_\lambda$. This implies that situations like the ones illustrated in FIGS. 6 and 7 may be difficult to handle. Neither is it possible to to derive information on the structural properties of the water/ice layer on the road surface using the methods described above. All embodiments shown should however be interpreted as illustrative only, and not as limiting.

In the examples presented above, the surface conditions are concluded by detecting the reflectance properties at two or three wavelengths, but obviously any number of wavelengths may be used. Further, only the signals $S_1$ and $S_2$ are discussed, but obviously $S_0$ and $S_3$, $S_4$ . . . etc. may be used to support the surface property identification algorithms.

The three embodiments shown have a light beam emitter 1, 3, 5 and a wavelength selective system, where the latter acts to select suitably chosen wavelengths and wavelength modulate these before or after the beam is reflected by the road surface. The light beam emitter may use an incandescent lamp, an LED or, if sufficient background light is present, may be eliminated altogether. Wavelength selective systems using prisms, gratings or dielectric filter are shown, but other solutions are possible such as acousto optic modulators, which may have a much higher modulation frequency than any mechanical solution. Alternatively, the light beam emitter and the wavelength selective system may be integrated into a single functional unit using a wavelength modulated laser source.

The detection device may be mounted in a vehicle such that it may detect ice or water under the vehicle, but may alternatively be forward looking, giving the driver an advance warning of upcoming wet or icy sections of the road. For such a forward looking detection device further functionality may be integrated into the system, for example a system which makes the detection device track the road in front of the vehicle as the road turns, or have two or several detection areas, such as one nearer and another further from the front of the vehicle.

The detection device is intended to be part of a system for determining the road surface condition including a road surface indicator, preferably mounted in the vehicle compartment. The road surface indicator shows the present road surface condition and may warn at sudden changes in road surface conditions.

Although the invention has been described in conjunction with a number of preferred embodiments, it is to be understood that various modifications may still be made without departing from the scope of the invention as defined by the appended claims. One such modification is to use the invention for determining the surface condition of objects other than roads.

The invention claimed is:

1. A device for determining a surface condition, said device comprising a reflectance spectrometer which is arranged to sense the reflectance properties of a surface at at least one wavelength and using said reflectance properties to determine the presence of at least one of liquid water or ice, characterised in that said reflectance spectrometer is a wavelength modulation spectrometer which modulates the wavelength of light at a frequency f, said wavelength modulation spectrometer being provided with means to detect the resulting amplitude modulation at more than one multiple of said frequency f.

2. A device for determining a surface condition according to claim 1, characterised in that said wavelength modulation spectrometer comprises a wavelength selective system arranged to select and wavelength modulate light of at least one wavelength, where said wavelength selective system comprises at least one of a chopper wheel, a tuning fork optical chopper, a dispersive prism, a grating, an acousto optic modulator or a dielectric filter.

3. A device for determining a surface condition according to claim 1, characterised in that said wavelength modulation spectrometer comprises a wavelength modulated laser.

4. A system for determining and indicating a surface condition, said system comprising a device for determining a surface condition according to claim 1, and comprising an indicator device for indicating the road surface condition determined by said device for determining a surface condition.

5. A method for determining a surface condition, said method using reflectance spectrometry for sensing the reflectance properties of a surface at at least one wavelength and using said reflectance properties to determine presence of at least one of liquid water or ice, characterised in that said reflectance spectrometry is wavelength modulation spectrometry, where the wavelength of the light is modulated at a frequency f, and the resulting amplitude modulation is detected at more than one multiple of said frequency f.

6. A method for determining a surface condition according to claim 5, characterised in that light of said at least one wavelength is wavelength modulated before being reflected by said surface.

7. A method for determining a surface condition according to claim 5, characterised in that light of said at least one wavelength is wavelength modulated after being reflected by said surface.

8. A method for determining a surface condition according to claim 5, characterised in that light of said at least one wavelength also is intensity modulated.

9. A method for determining a surface condition according to claim 5, characterised in that said method senses the reflectance properties of a surface at more than one wavelength.

10. A method for determining a surface condition according to claim 9, characterised in that said method uses the reflectance properties at the more than one wavelengths to determine the structural properties of the detected liquid water or ice.

* * * * *